United States Patent [19]
Gillet et al.

[11] Patent Number: 5,643,947
[45] Date of Patent: Jul. 1, 1997

[54] ω-AMINO-α-PHENYLALKANONITRILE DERIVATIVES

[75] Inventors: Claude L. Gillet, Blanmont, Belgium; Philippe R. Bovy, St. Louis, Mo.; Hugo Gorissen, Grez Doiceau; Michel P. Snyers, Limal, both of Belgium

[73] Assignee: G. D. Searle & Co., Skokie, Ill.

[21] Appl. No.: 448,911

[22] Filed: May 24, 1995

Related U.S. Application Data

[63] Continuation of Ser. No. 40,824, Mar. 31, 1993, abandoned, which is a continuation of Ser. No. 811,450, Dec. 19, 1992, abandoned, which is a continuation of Ser. No. 638,006, Jan. 5, 1991, abandoned, which is a continuation of Ser. No. 454,341, Dec. 21, 1989, abandoned.

[51] Int. Cl.$^6$ .................. C07K 255/24; A61K 31/275
[52] U.S. Cl. ............................................. 514/523; 558/390
[58] Field of Search ........................ 538/408; 558/390; 514/523

[56] References Cited

U.S. PATENT DOCUMENTS

| | | | |
|---|---|---|---|
| 4,612,329 | 9/1986 | Itoh et al. | 514/523 |
| 4,681,970 | 7/1987 | Liang | 558/408 |

FOREIGN PATENT DOCUMENTS

| | | | |
|---|---|---|---|
| 0257768 | 3/1988 | European Pat. Off. | |
| 2263527 | 12/1971 | Germany | |
| 50-71644 | 6/1975 | Japan | 558/408 |
| 1192625 | 5/1970 | United Kingdom | |

OTHER PUBLICATIONS

Blicke, et. al.; J. Org. Chem., 26, (1961), pp. 1826–1831.
DeFeudis, DN & P, 2 (1989), pp. 113–114.

*Primary Examiner*—Robert Gerstl
*Attorney, Agent, or Firm*—Joseph W. Bulock

[57] ABSTRACT

A class of ω-amino-α-phenylalkanonitrile derivatives is described having use in treatment of cardiovascular dysfunctions such as hypertension. Compounds of most interest are those of the formula:

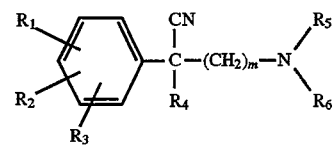

wherein each of $R_1$ and $R_2$ is methoxy, $R_3$ is hydrido, $R_4$ is isopropyl, $R_5$ is methyl and $R_6$ is selected from linear alkyl, phenylpropyl, phenylbutyl and phenylpentyl.

9 Claims, No Drawings

ω-AMINO-α-PHENYLALKANONITRILE DERIVATIVES

RELATED CASES

This is a continuation of application Ser. No. 040,824, filed Mar. 31, 1993, now abandoned, which is a continuation of 07/811,450, filed Dec. 19, 1992, now abandoned, which is a continuation of 07/638,006 filed Jan. 5, 1991, now abandoned, which is a continuation of application Ser. No. 07/454,341 filed Dec. 21, 1989, now abandoned.

BACKGROUND OF THE INVENTION

Calcium channel antagonist compounds are known for use in treatment of cardiovascular disorders. These compounds inhibit smooth and cardiac muscle contraction by blocking the influx of calcium ions through plasma membrane channels. Drugs based on such compounds are widely used in the treatment of a variety of cardiovascular disorders, including arrhythmia, infarction, angina and hypertension. Examples of such drugs are verapamil, nifedipine and diltiazem.

Verapamil and related analogues are structurally characterized by the presence of a 5-amino-2-phenylvaleronitrile moeity which is dialkylated on the amino group. Such compounds are further characterized by the presence of a phenylethyl fragment as substituent on the amino group. Examples of such "verapamil-type" compounds are gallopamil, tiapamil, falipamil, anipamil and desmethoxyverapamil.

Other valeronitrile derivatives have also been described. For example, the synthesis of 5-(dibutylamino)-2-phenylvaleronitriles has been reported [F. F. Blicks et. al, *J. Org. Chem.*, 26, 1826 (1961)]. A series of Japanese patents (JAPatent 033118, 1975; JA Patent 033703, 1973) describes valeronitrile derivatives with coronary vasodilating inhibition activity.

A verapamil-like compound has been evaluated for properties other than calcium channel blocking activity. For example, the compound (S)-emopamil has been found to act as an antagonist at serotonin-2 ($5\text{-HT}_2$) receptors of both blood vessels and brain, as well as showing calcium channel blocking activity [F. V. DeFeudis, *DN & P*, 2 (2), 113–114 (March 1989)].

DESCRIPTION OF THE INVENTION

Treatment of a mammal afflicted with or susceptible to a cardiovascular disorder, such as hypertension and related diseases like angina, certain types of arrhythmias and microcirculation dysfunction, is provided by administering to the mammal a therapeutically-effective amount of a compound selected from a class of ω-amino-α-phenylalkanonitrile compounds defined by Formula I:

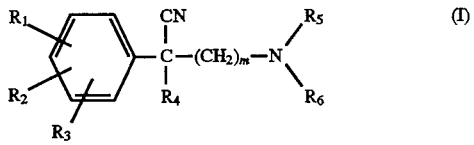

wherein each $R_1$, $R_2$ and $R_3$ is independently selected from hydrido, hydroxyl, alkyl, halo, alkoxy, alkylthio and alkylsulfinyl; wherein $R_4$ is a linear, branched or cyclic alkyl radical having three to about six carbon atoms; wherein each of $R_5$ and $R_6$ is independently selected from hydrido, linear or branched alkyl or alkenyl radical of three to about twelve carbon atoms, which alkyl or alkenyl radical may be substituted with a phenyl radical, and said phenyl radical may be further substituted by one or more groups selected from hydroxyl, alkyl, alkenyl, halo, alkoxy, alkoxycarbonyl, aminocarbonyl, alkylaminocarbonyl, dialkylaminocarbonyl, alkylcarbonylalkyl, alkylcarbonylalkenyl, alkylthio, alkylsulfinyl and alkylsulfonyl; wherein m is a number selected from three to five, inclusive; with the proviso that when one of $R_5$ and $R_6$ is phenylalkyl substituted by alkyl substituent, then said alkyl substituent cannot be attached at the ortho position of the phenyl ring of said phenylalkyl; or a pharmaceutically acceptable salt thereof.

A preferred family of compounds consists of the compounds of Formula I wherein each $R_1$, $R_2$ and $R_3$ is independently selected from hydrido, hydroxyl, alkyl, halo, alkoxy, alkylthio and alkylsulfinyl; wherein $R_4$ is a linear, branched or cyclic alkyl radical having three to about six carbon atoms; wherein each of $R_5$ and $R_6$ is independently selected from hydrido, linear or branched alkyl or alkenyl radical of three to about twelve carbon atoms, which alkyl or alkenyl radical may be substituted with a phenyl radical, and said phenyl radical may be further substituted by one or more groups selected from hydroxyl, alkyl, alkenyl, halo, alkoxy, alkylthio, alkylsulfinyl and alkylsulfonyl; wherein m is a number selected from three to five, inclusive; with the proviso that when either of $R_5$ or $R_6$ is hydrido or benzyl, then the other of $R_5$ and $R_6$ cannot be methyl, with the further proviso that $R_5$ and $R_6$ cannot simultaneously be selected from hydrido, methyl, ethyl, n-propyl and isopropyl, and with the further proviso that when one of $R_5$ and $R_6$ is phenylalkyl substituted by alkyl substituent, then said alkyl substituent cannot be attached at the ortho position of the phenyl ring of said phenylalkyl; or a pharmaceutically acceptable salt thereof.

A more preferred family of compounds consists of those compounds of Formula I wherein each $R_1$, $R_2$ and $R_3$ is independently selected from hydrido, hydroxyl, alkyl, halo, alkoxy and alkylthio; wherein $R_4$ is a linear, branched or cyclic alkyl radical having three to about six carbon atoms; wherein each of $R_5$ and $R_6$ is independently selected from hydrido, linear or branched alkyl or alkenyl radical of three to about twelve carbon atoms, which alkyl or alkenyl radical may be substituted with a phenyl radical, and said phenyl radical may be further substituted by one or more groups selected from hydroxyl, alkyl, alkenyl, halo, alkoxy and alkylthio; wherein m is a number selected from three to five, inclusive; with the proviso that when either of $R_5$ or $R_6$ is hydrido or benzyl, then the other of $R_5$ and $R_6$ cannot be methyl, with the further proviso that $R_5$ and $R_6$ cannot simultaneously be selected from hydrido, methyl, ethyl, n-propyl and isopropyl, and with the further proviso that when one of $R_5$ and $R_6$ is phenylalkyl substituted by alkyl substituent, then said alkyl substituent cannot be attached at the ortho position of the phenyl ring of said phenylalkyl; or a pharmaceutically acceptable salt thereof.

A highly preferred claim of compounds consists of those compounds of Formula I wherein each $R_1$, $R_2$ and $R_3$ is independently selected from hydrido, hydroxyl, alkyl, halo and alkoxy; wherein $R_4$ is a linear, branched or cyclic alkyl radical having three to about five carbon atoms; wherein each of $R_5$ and $R_6$ is independently selected from hydrido, linear or branched alkyl or alkenyl radical of three to about ten carbon atoms, which alkyl or alkenyl radical may be substituted with a phenyl radical, and said phenyl radical may be further substituted by one or more groups selected from hydroxyl, alkyl, halo and alkoxy; wherein m is a number selected from three to five, inclusive; with the proviso that when either of $R_5$ or $R_6$ is hydrido or benzyl, then the other of $R_5$ and $R_6$ cannot be methyl, with the further proviso that $R_5$ and $R_6$ cannot simultaneously be selected from hydrido, methyl, ethyl, n-propyl and isopropyl, and with the further proviso that when one of $R_5$ and $R_6$ is phenylalkyl substituted by alkyl substituent, then said alkyl substituent cannot be attached at the ortho position of the phenyl ring of said phenylalkyl; or a pharmaceutically acceptable salt thereof.

A more highly preferred class of compounds consists of those compounds of Formula I wherein each $R_1$ and $R_2$ is independently selected from lower alkoxy; wherein $R_3$ is hydrido; wherein $R_4$ is a linear or branched alkyl radical having three to four carbon atoms; wherein each of $R_5$ and $R_6$ is independently selected from linear or branched alkyl radical of three to about ten carbon atoms, which alkyl radical may be substituted with a phenyl radical; wherein m is a number selected from three to five, inclusive; with the proviso that when either of $R_5$ or $R_6$ is benzyl, then the other of $R_5$ and $R_6$ cannot be methyl, with the further proviso that $R_5$ and $R_6$ cannot simultaneously be selected from methyl, ethyl, n-propyl and isopropyl; or a pharmaceutically acceptable salt thereof.

The compounds of this invention are novel derivatives of ω-amino-α-phenylalkanonitrile characterized by the presence of a straight or branched alkyl chain on the amino group, which alkylchain has a linear chain of at least three carbons. These compounds show potent anticalcic properties and have lower toxicity than verapamil itself. In addition, an unexpected enhancement of binding of the compounds of the invention to the serotonin receptor over that of verapamil has been obtained. Thus, the compounds of Formula I having a profile combining calcium antagonistic action, increased antagonistic action on $5HT_2$ receptor and low toxicity should provide antihypertensive agents of superior therapeutic utility.

The term "hydrido" denotes a single hydrogen atom (H) which may be attached, for example, to a carbon atom to form hydrocarbyl or methylene, or attached to an oxygen atom to form a hydroxyl group. Where the term "alkyl" is used, either alone or within other terms such as "haloalkyl", "aralkyl" and "hydroxyalkyl", the term "alkyl" embraces linear or branched radicals having one to about twenty carbon atoms. Preferred alkyl radicals are "lower alkyl" radicals having one to about ten carbon atoms. Examples of which include methyl, ethyl, n-propyl, isopropyl, n-butyl, sec-butyl, iso-butyl, tert-butyl, n-pentyl, neopentyl, n-hexyl, 1-methylhexyl, n-heptyl, 2-ethylheptyl, n-octyl, n-nonyl, n-decyl and the like. The terms "cycloalkyl" and "cyclic alkyl" embrace radicals having three to ten carbon atoms, such as cyclopropyl and cyclobutyl. "Alkylcycloalkyl" means a cyclized alkyl having from four to about nine ring carbon atoms being substituted with an alkyl group, preferably a lower alkyl group. The term "haloalkyl" embraces radicals wherein any one or more of the carbon atoms is substituted with one or more halo groups, preferably selected from bromo, chloro and fluoro. Specifically embraced by the term "haloalkyl" are monhaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or my have a combination of different halo groups. A dihaloalkyl group, for example, may have two bromo atoms, such as dibromomethyl group, or two chloro atoms, such as a dichloromethyl group, or one bromo atom and one chloro atom, such as bromochloromethyl group. Examples of a polyhaloalkyl are trifluoromethyl, 2,2,2-trifluoroethyl, perfluoroethyl and 2,2,3,3-tetrafluoropropyl groups. The term "aryl" embraces aromatic radicals such as phenyl, biphenyl and naphthyl. The term "aralkyl" embraces aryl-substituted alkyl radicals such as benzyl, diphenylmethyl and triphenylmethyl. The terms "benzyl" and "phenylmethyl" are interchangeable. The term "alkoxy" embraces linear or branched oxy containing radicals having an alkyl portion of one to about ten carbon atoms, such as methoxy, ethoxy, isopropoxy and butoxy. The term "alkylthio" embraces radicals containing a linear or branched alkyl group of one to about ten carbon atoms attached to a divalent sulfur atom, such as a methythio group. The terms "aryloxy" and "arylthio" denote, respectively, aryl groups having an oxygen or sulfur atom through which the radical is attached to a nucleus, examples of which are phenoxy and phenylthio. The terms "sulfinyl" and "sulfonyl", whether used alone or linked to other terms, denote respectively, divalent radicals SO and $SO_2$. The term "acyl" whether used alone, or within a term such as acyloxy, denotes a radical provided by the residue remaining after removal of hydroxy from an organic acid, examples of such radical being lower alkanoyl, such as acetyl and benzoyl. The term "alkenyl" embraces linear or branched radicals having two to about twenty carbon atoms, preferable three to about ten carbon atoms, and containing at least one carbon-carbon double bond. The term "alkoxyalkyl" embraces linear or branched radicals each having two alkyl portions of one to about ten carbon atoms spaced apart by an oxy-containing radical, such as methoxymethyl group. The "alkoxy" or "alkoxyalkyl" radicals may be further substituted with one or more halo atoms, such as fluoro, chloro or bromo, to provide haloalkoxy or haloalkoxyalkyl groups.

Within this class of compounds of the invention are the pharmaceutically acceptable salts of the compounds of Formula I, including acid addition salts and base addition salts. The term "pharmaceutically-acceptable salts" embraces "pharmacologically-acceptable salts" commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from calcium, lithium, magnesium, potassium, sodium and zinc, or organic salts made from N,N'-dibenzylethlenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of Formula I have been found to inhibit smooth muscle and cardiac muscle contraction by blocking influx of calcium ions through plasma membrane channels. Thus, compounds of Formula I are therapeutically useful in methods for treating hypertension by administering to a hypertensive patient a therapeutically-effective amount of a compound of Formula I. The phrase "hypertensive patient" means, in this context, a mammalian subject suffering from the effects of hypertension or susceptible to a hypertensive condition if not treated to prevent or control such hypertension.

The compounds of the invention can be formulated into pharmaceutically-acceptable dosage forms by any of a number of well-known carriers or diluents. The compounds can be formulated using pharmaceutically-acceptable acid addition salts which are pharmacologically-acceptable and which can be used in a suitable hydrated form. The formulated compounds can be administered in oral dosage forms such as tablets, capsules, pills, powders, or granules. The compounds can also be administered intramuscularly, using forms known to the pharmaceutical art. In general, the preferred form of administration is oral. A therapeutically effective but non-toxic quantity of the compound is employed in treatment of high blood pressure in mammals. The dosage regimen for preventing or treating hypertension with the compounds of Formula I is selected upon consideration of a variety of factors including the age, weight, sex and medical condition of the patient, the severity of the hypertension, the route of administration, and the particular compound employed. Dosages of active compounds are ordinarily in the range from about 0.5 to about 100 mg/kg (active compound-to-body weight), and preferably from about 1.0 to about 20 mg/kg given orally or by injection.

GENERAL SYNTHETIC PROCEDURES

Compounds within Formula I can be synthesized in accordance with the following general procedures wherein for each formula shown the substitution pattern for $R_1$, $R_2$, $R_3$, $R_4$, $R_5$ and $R_6$ is as defined before, $R_7$ has the value of $R_6$ with one carbon atom less, and X is halo.

Compounds of the invention may be synthesized by reacting a phenylacetonitrile derivative II with a reactant of structure $R_4$ X, wherein X is preferably halo such as bromo or chloro, to obtain an ω-substituted phenylalkanonitrile III (step 1) which is then reacted with a compound of general structure $X(CH_2)$ m $NR_5R_6$ to give compounds of general structure I (step 3).

Steps 1 and 3 are best conducted in the presence of a strong base, such as sodium amide or sodium hydride, in an aprotic solvent such as benzene, toluene, and tetrahydrofuran or in ammonia. Compounds of the invention may also be synthesized by reacting an w-substituted phenylalkanonitrile III with a reactant $X(CH_2)_m$ X wherein X has the same value as above to obtain a compound of structure IV (step 2) which is reacted with a secondary amine $R_5R_6$ NH to give compounds of general structure I (step 4). Step 2 is best conducted in experimental conditions already described for steps 1 and 3. Step 4 is best carried out in aprotic solvent such as benzene and toluene or without solvent in the presence of a base such as diisopropylethylamine.

Compounds of the invention may also be synthesized by reacting compound IV with a primary amine $R_5NH_2$ to obtain a compound of structure V (step 5) which is reacted with an aldehyde ($R_7CHO$) or an acid ($R_7COOH$) to give compounds of general structure I (step 6). Step 5 is conducted in the same conditions as for step 4. Step 6 is best carried out in an aprotic solvent such as tetrahydrofuran or toluene, with a reducing agent such as sodium borohydride or hydrogen.

The following Examples are detailed descriptions of the methods of preparation of compounds of Formula I. These detailed preparations fall within the scope of, and serve to exemplify, the above described General Synthetic Procedures which form part of the invention. These Examples are presented for illustrative purposes only and are not intended as a restriction on the scope of the invention. All parts are by weight unless otherwise indicated.

EXAMPLE #1

5-[(n-octyl) methylamino]-2-(3,4-dimethoxyphenyl) -2-isopropyl-valeronitrile (Compound #1).

Procedure A

In a 250 ml flask under a nitrogen atmosphere, a mixture of 25.2 g (0.175 mol) of octanoic acid, 70 ml of THF, 2.3 g of 5-(methylamino)-2-(3,4-dimethoxyphenyl)-2-

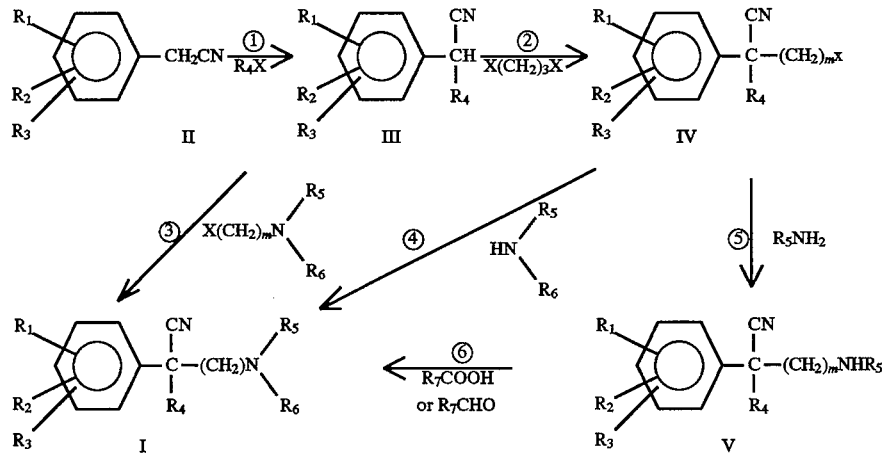

isopropylvaleronitrile and 0.6 g of sodium acetate was heated with stirring at 50°–55° C. and 1.5 g (0.038 mol) of sodium borohydride was added portion-wise. The mixture was stirred at 50°–55° C. for 20H. After cooling, 100 mg of water was added and the solution cooled in an ice-bath was made basic by addition of solid NaOH. The mixture was extracted with $Et_2O$ and then the organic phase extracted with 2N HCl (4 times). The combined aqueous solutions were made basic with solid NaOH and extracted with Et$_2$O. The extract was washed with water and with a saturated NaCl solution and worked up to give an oil, which was chromatographed on a SiO$_2$ column. Elution with CH$_3$OH / CHCl$_3$ (5 : 95) gave 0.8 g of Compound #1 as a colorless oil. Anal. calcd. for C$_{25}$H$_{42}$N$_2$O$_2$: C, 74.58; H, 10.51; N, 6.96; Found C, 74; H, 10.72; C, 6.98.

Procedure B

In a 250 ml flask equipped with a Dean-Stark water separator, a mixture of 4.2 g (0.0145 mol) of 5-(methylamino)-2-(3,4-dimethoxyphenyl)-2-isopropylvaleronitrile, 2 g (0.0159 mol) of n-octaldehyde and 100 ml of toluene were heated under reflux for 2H with continuous removal of water. After solvent evaporation, the yellow oily residue was diluted with 300 ml EtOH and 1 ml AcOH and hydrogenated for 2H in the presence of 50 mg PtO$_2$ in a Parr Apparatus at an initial pressure of 1900 mbar. After removal of the catalyst, the solution was evaporated in vacuo to obtain 7.1 g of a yellow oil. The oil was washed twice with hot pentane and chromatographed on a SiO$_2$ column. Elution with CH$_3$OH CHCl$_3$ (5 : 95) gave 1.7 g of Compound #1 as a colorless oil. Anal. calcd. for C$_{25}$H$_{42}$H$_2$O$_2$: C, 74.53; H, 10.51; N, 6.96. Found: C, 74.03; H, 10.63; N, 7.13. $^1$H NMR (CDCl3) δ 0.79 (3H, d, CH$_3$ isopropyl), δ 0.87 (3H, t,CH$_3$–CH$_2$) δ 1.18 (3H, d, CH$_3$ isopropyl), δ 1.25 (10H, m, CH$_2$ inside chain), δ 1.25–1.90 (6H, m, CH$_2$ others), 2.07 (3H, s,CH$_3$—N), δ 2.21 (5H, m, CH$_2$—N, CH isopropyl), δ 3.88 (6H, s,OCH$_3$), δ 6.82–6.91 (3H, m, aromatics).

EXAMPLE #2

5-[(4-phenylbutyl)methylamino]-2-(3,4-dimethoxyphenyl)-2-isopropylvaleronitrile (Compound #2).

In a 250 ml flask under a nitrogen atmosphere, a mixture of 41 g (0.25 mol) of 4-phenylbutanoic acid, 70 ml of THF, 3.3 g of 5-(methylamino)-2-(3,4-dimethoxyphenyl)-2-isopropylvaleronitrile and 820 mg of sodium acetate was heated with stirring at 50°–55° C. and 2.1 g (0.55 mol) of NaBH$_4$ was added portion-wise. After cooling, 100 ml of water was added and the solution cooled in an ice-bath was made basic by addition of solid NaOH. The mixture was extracted with Et$_2$O. The extract was washed with water and with a saturated NaCl solution and worked up to give a yellow oil. This oil was dissolved in isopropanol and treated with a solution of oxalic acid in isopropanol to give 2.1 g of the oxalate salt of Compound #2 as a white powder, mp: 116°–117° C. Anal. calcd. for C$_{27}$H$_{38}$N$_2$O$_2$·C$_2$H$_2$O$_4$: C, 67.35; H, 7.89; N, 5.42 Found C, 67.26; H, 7.96; N, 5.42. $^1$H NMR (CDCl$_3$)δ 0.79 (3H, d, CH$_3$ isopropyl), δ 0.87 (3H, t,CH$_3$–CH$_2$) δ 1.18 (3H, d, CH$_3$ isopropyl), δ 1.25 (14H, m, CH$_2$ inside chain), δ 7.25–1.90 (6H, m, CH$_2$ others) 2.07 (3H, s, CH$_3$—N), δ 2.21 (5H,m, CH$_2$—N, CH isopropyl), δ 3.88 (6H, s,OCH$_3$), δ 6.82–6.91 (3H,m, aromatics).

The following Compounds #2–8 were synthesized using the methods described for the General Synthetic Procedures and the methods described in Example #1 and #2. Compound analytical data are reported in Table I.

Compound #

3  5-[5-(phenylpentyl)methylamino]-2-(3,4-dimethoxyphenyl)-2-isopropylvaleronitrile 4  for 5-[5-(phenylpentyl)methylamino]-2-(3,4-dimethoxyphenyl) -2-isopropylvaleronitrile 5  5-[(n-octyl)benzylamino]-2-(3,4-dimethoxyphenyl-2-isopropylvaleronitrile 6  5-[(n-decyl)methylamino]-2-(3,4-dimethoxyphenyl)-2-isopropylvaleronitrile 7  for 5-[(4-(3,4-dimethoxyphenylbutyl) methylamino-[2-(3,4-dimethoxyphenyl)-2-isopropyl-valeronitrile 8  for 5-[(3-(3,4-dimethoxyphenylpropyl)methyl-amino [2-(3,4-dimethoxyphenyl)-2-isopropyl-valeronitrile

TABLE I $$\begin{array}{c} R_1 \\ R_2 \end{array} \diagdown \bigcirc \diagdown \begin{array}{c} CN \\ | \\ C-(CH_2)_3-N \\ | \\ R_4 \end{array} \diagdown \begin{array}{c} R_5 \\ \\ R_6 \end{array}$$
(with R$_3$ on ring)

| Compound # | R$_1$ | R$_2$ | R$_3$ | R$_4$ | R$_5$ | R$_6$ | mp (°C.) | C calc | C found | H calc | H found | N calc | N found |
|---|---|---|---|---|---|---|---|---|---|---|---|---|---|
| 1 | CH$_3$O | CH$_3$O | H | isoC$_3$H$_7$ | CH$_3$ | —(CH$_2$)$_7$CH$_3$ | oil | 74.58 | 74.58 | 10.51 | 10.72 | 6.96 | 6.98 |
| 2 | CH$_3$O | CH$_3$O | H | isoC$_3$H$_7$ | CH$_3$ | —(CH$_2$)$_4$—C$_6$H$_5$ | 116–117 (oxalate) | 67.35 | 67.26 | 7.89 | 7.96 | 5.42 | 5.42 |
| 3 | CH$_3$O | CH$_3$O | H | isoC$_3$H$_7$ | CH$_3$ | —(CH$_2$)$_5$—C$_6$H$_5$ | 90–91 (oxalate) | 68.42 | 67.98 | 8.04 | 8.05 | 5.32 | 5.32 |
| 4 | CH$_3$O | CH$_3$O | H | isoC$_3$H$_7$ | CH$_3$ | —(CH$_2$)$_3$—C$_6$H$_5$ | 133–134 (oxalate) | 67.45 | 67.46 | 7.68 | 7.76 | 5.62 | 5.67 |
| 5 | CH$_3$O | CH$_3$O | H | isoC$_3$H$_7$ | CH$_2$—C$_6$H$_5$ | —(CH$_2$)$_7$CH$_3$ | oil | 77.78 | 77.53 | 9.69 | 9.80 | 5.85 | 5.78 |
| 6 | CH$_3$O | CH$_3$O | H | isoC$_3$H$_7$ | CH$_3$ | —(CH$_2$)$_9$CH$_3$ | oil | 75.30 | 75.44 | 10.77 | 11.03 | 6.51 | 6.40 |

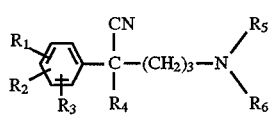

TABLE I-continued $$R_1\text{-}\underset{R_2}{\overset{}{\bigcirc}}\text{-}\underset{R_3}{\overset{CN}{\underset{|}{C}}}\text{-}(CH_2)_3\text{-}N\underset{R_6}{\overset{R_5}{\diagup}}$$

| Compound # | $R_1$ | $R_2$ | $R_3$ | $R_4$ | $R_5$ | $R_6$ | mp (°C.) | C calc | C found | H calc | H found | N calc | N found |
|---|---|---|---|---|---|---|---|---|---|---|---|---|---|
| 7 | $CH_3O$ | $CH_3O$ | H | $isoC_3H_7$ | $CH_3$ | $-CH_2-CH=CH-\bigcirc$ | 50–55 (maleate) | 62.32 | 62.73 | 7.19 | 7.18 | 4.54 | 4.52 |
| 8 | $CH_3O$ | $CH_3O$ | H | $isoC_3H_7$ | H | $-(CH_2)_7CH_3$ | 155–156 (oxalate) | 64.03 | 64.40 | 8.88 | 8.84 | 5.74 | 5.73 |

BIOLOGICAL DATA

Calcium channel blockers of this invention would be expected to induce vasodilation, prevent vasoconstriction, lower heart rate and myocardial contractibility, prevent several types of arrhythmias, lower high blood pressure, protect against myocardial ischemia, reduce myocardial infarct size and possibly protect against cerebral anoxia and ischemia. The coexistence of additional properties like blockade of $a_1$ adrenergic receptors adds to the therapeutic potential of these molecules. The compounds of the invention combine a $Ca^{2+}$ channel blocking activity with a high affinity for the serotonin receptor ($5HT_2$). Also, some compounds of the invention additionally possess $\alpha_1$—adrenergic receptor affinity.

Table II contains biological data obtained for eight compounds of the invention. Receptor binding experiments were conducted under the experimental conditions described in Table III. $^3$H-nitrendipine is the radioligand of choice to determine, after competition at different concentrations, the affinity of compounds of the invention, for the slow $Ca^{2+}$ channel binding sites. All the compounds of the invention were found in this binding study to interact with the slow channel $Ca^{2+}$ binding sites. Compounds #1, #2, #4 and #7 interact with the slow $Ca^{2+}$ channel binding sites by displaying an apparent competition curve that does not reach the non-specific base-line. In contrast, Compounds #3, #5, #6 and #8 display binding profiles having apparent competition curves reaching the non-specific level. After this in vitro biochemical testing, the compounds of the invention were tested for their $CA^{2+}$ antagonist properties on isolated organs. The method used was updated from M Spedding (Nauyn-Schmiedeberg's Arch. Pharmacol., 318, 234–240, 1982) and can be summarized as follows: Aorta rings from male rats were prepared and maintained in oxygenated Krebs solution at 37° C. The contractions were induced by 40 mM K+ in the absence or in the presence of the test compound. Each test compound was tested at least twice. For each compound inhibiting the K+ response by at least 50% at 1 mcM, an $IC_{50}$ was determined by testing on the same preparation three concentrations giving about 25, 50 and 75% inhibition. The phasic and tonic parts of each response elicited by K+ were considered separately and were expressed in % of their corresponding controls. The $IC_{50}$ values (from pIC50) were estimated by plotting the % response against the log of the concentrations.

As shown in Table II, Compounds #1 and #2 inhibited the contractions induced by 40 mMK+ at rather low concentrations. Concentrations inhibiting the contractions by 50% were of 200 nM and 60 nM, respectively. The phasic and tonic phases of the contractions were similarly inhibited. The $Ca^{2+}$ antagonist properties were confirmed by the evaluation of vasodilation in the perfused hindlimb dog model. The peripheral vasodilator activity of compounds of the invention was measured in anaesthetized dog at the femoral arterial circulation. For this procedure, the femoral artery (the collaterals of which were ligated) was perfused with a constant flow rate of blood taken from aorta. The perfusion pressure measured at the femoral artery varied as a function of the resistance of the perfused area. The test compounds in diluted solvents were directly injected in the system at a dose of 30 mcg/kg. With the blood circulation rate being maintained constant, vasodilation was thus measured by a decrease of the perfusion pressure, in comparison with the action of papaverine considered as standard. The vasodilator activity was rated as follows:

0: reduction <10 mmHg.

+: ⅓ of the papaverine activity.

++: ⅔ of the papaverine activity.

+++: activity equal to that of papaverine (i.e. 30 to 40 mm Hg).

++++: activity higher than that of papaverine.

Compounds #1 and #2 were found to be more active than papaverine.

The biological activity of the compounds of the invention was evaluated in vivo on spontaneous hypertensive rats. In this test, antihypertensive activity was tested by oral administration to non-anaesthetized, spontaneously hypertensive rats, on which the systolic arterial pressure was measured at the median coccygeal artery by means of a plethysmographic method [J. Roba, G. Lambelin, A. F. De Schaepdryver, Arch. Int. Pharmacodyn., 200, 182 (1972)]. The arterial pressure was measured every 30 minutes from two hours before to three hours after oral administration of 60 mg/kg of the test compounds or of a placebo (1% tragacanth gum mucilage). Only rats having a systolic pressure of 180 to 220 mmHg were used. Each compound was tested in two rats.

The antihypertensive effects were rated as follows:

0: reduction <10 mm Hg.

+: reduction of 10 to 20 mm Hg.

++: reduction of 20 to 30 mm Hg.

+++: reduction of 30 to 40 mm Hg.

++++: reduction >40 mm Hg.

Compounds #1 and #2 were found in this model to induce the maximal antihypertensive effect by lowering the systolic blood pressure by more than 40 mm Hg.

The compounds of the invention were tested in receptor binding using $^3$H-ketanserin as radioligand on frontal cortex preparations of rat, using a procedure summarized in Table III. These binding studies have demonstrated specificity for the $5HT_2$ serotonin receptor subpopulation. The experimental conditions are summarized in Table III. Compounds #1–4 and #6–8 were found to have an affinity for the $5HT_2$ receptor higher than the compound verapamil.

Compounds #2, #7 and #8 were found to display affinity for the $\alpha_1$-adrenergic receptor, identified by the $^3$H-WB4101 binding on rat forebrain cell membrane preparation. The experimental conditions of this binding are summarized in Table III.

Compounds #1, #2, #3, #4 and #7 were tested for acute toxicity. The acute toxicity was determined after oral administration of the test compound to mice. Compound to be tested was suspended in a 1% tragacanth gum mucilage and was administered by means of an intragastric tube to a group of three male mice per dose. The mortailty was recorded over a period of 15 days. The $LD_{50}$ results in Table II were calculated according to published methods (Litchfield and Wilcoxon, J. Pharmacol., Exp, The., 96, 99, 1949) and expressed in mg of test compound per kilogram body weight of mouse. All tested compounds were found to display $LD_{50}$ values greater than 300 mg/kg., and are therefore 2 to 3 times less toxic than verapamil.

In conclusion, some of the compounds of the invention were shown to possess a high affinity for the $Ca^{2+}$ channel receptor. Such compounds were able to antagonize contractions of arterial preparations due to the $CA^{2+}$ entry in vitro, and displayed a potent vasodilating activity, after intra-arterial administration in dogs and in antihypertensive rats. Such high affinity for the $5HT_2$ and $\alpha_1$-receptors, in absence of vasoconstricting activity in vitro and in vivo, is therefore indicative of an antagonistic effect at these receptors. Furthermore, the lack of affinity for the histaminic $H_1$ receptor binding sites labelled by $^3$H-pyrylamine [S. J. Hill et al, Brit. J. Pharmacol., 68, 687 (1980)] indicates that the effect of the compounds of the invention on the $Ca^{2+}$, $5HT_2$ and $\alpha_1$-adrenergic receptors is selective. The combination of $5HT_2$ and $\alpha_1$-blocking activity, along with $Ca^{2+}$ channel blocking activity of the compounds of the invention, presents an advantage for the treatment of high blood pressure and allied cardiovascular disorders.

TABLE II

Biological Evaluation of Compounds of the Invention

| No | CA2+ BINDING pKi | AORTA/K+ pIC50 phasic/tonic | VASODILATION score | SHR score | 5HT2 pKi | α1 pKi | LD50 mg/kg |
|---|---|---|---|---|---|---|---|
| 1 | A (1) | 6.7/6.7 | ++++ | ++++ | 7 (2) | ≦6 | >300 |
| 2 | A (1) | 7.2/7.0 | ++++ | ++++ | 7 (2) | 7 (2) | 350 |
| 3 | 6.6 | N.T. | +++ | N.T. | 8 (2) | ≦6 | 470 |
| 4 | A (1) | N.T. | N.T. | N.T. | 7.5 (2) | ≦6 | 540 |
| 5 | 6.3 | N.T. | N.T. | N.T. | <6 | ≦6 | N.T. |
| 6 | 7.4 | ≦6 | N.T. | N.T. | 7 (2) | <6 | N.T. |
| 7 | A (1) | N.T. | N.T. | N.T. | 7 (2) | 6.8 (2) | >1000 |
| 8 | 6.9 | N.T. | N.T. | N.T. | 6.8 | 6.7 (2) | N.T. |

(1) A: Significant Activity; the non-specific level defined by 1 μM nifedipine could not be reached by 10 μM of the test-compound.
(2) Estimated values.
N.T. = Not tested.

TABLE III

Methodological Data for In Vitro Binding Assay of Various Receptors

| RECEPTORS | Ca2+ | 5HT2 | α1 |
|---|---|---|---|
| Tissues | | | |
| species | guinea-pig | rat | rat |
| dissected area | forebrain | frontal cortex | forebrain |
| mg wet w./assay. | 10.0 | 9.0 | 10.0 |
| working dilut.: v/w (ml/g) | 20 | 100 | 4 |
| ml dilut./assay | 0.20 | 0.90 | 0.04 |
| 3H-Ligand | | | |
| compound | nitrendipine | ketanserin | WB-4101 |
| final conc.: nM | 0.2 | 1.0 | 1.6 |
| KD ± SD(n): nM | 0.20 ± 0.02 (5) | 0.47 ± 0.05 (4) | 0.33 ± 0.16 (3) |
| working solut.: nM | 4 | 20 | 24 |
| ml solut./assay | 0.10 | 0.05 | 0.08 |
| Non-specific binding | | | |
| compound | nifedipine | methysergide | pentolamine |
| final conc.: nM | 1,000 | 1,000 | 1,000 |
| working solut.: nM | 20,000 | 20,000 | 10,000 |
| ml solut./assay | 0.10 | 0.05 | 0.12 |

TABLE III-continued

Methodological Data for In Vitro Binding Assay of Various Receptors

| RECEPTORS | Ca2+ | 5HT2 | α1 |
|---|---|---|---|
| Incubation conditions | | | |
| buffer | Tris-HCl 50 nM pH 7.4 | Tris-HCl 50 mM pH 7.7 | Tris-HCl 10 mM pH 7.4 MgCl2 10 mM |
| volume assay: ml | 2.0 | 1.0 | 1.2 |
| temperature: °C. | 25 | 37 | 25 |
| time: min | 90 | 15 | 15 |
| References | Murphy et. al. | Leysen et al. | Chatelain et al. |

K. N. M. Murphy et. al, Proc, Natl. Acad. Sci. USA, 80, 860 (1983).
J. E. Leysen et. al, Molec. Pharmacol., 21, 301 (1981).
Chatelain et. al, Arzneim. Forsch./Drug Res., 34II, 754 (1984).

$K_D$ values (Dissociation Constant) were determined by Scatchard analysis. $K_i$ values (Inhibition Constant) were calculated according to the Cheng and Prusoff equation, using $IC_{50}$ values:

$$K_i = \frac{IC_{50}}{1 + \frac{C}{K_D}}$$

The concentration of the drug producing a 50% inhibition of the specific binding ($IC_{50}$) was estimated graphically. The concentration (C) of the $^3$H-ligand used in the assay is given in Table III.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. Compound selected from compounds, and their pharmaceutically acceptable salts, of the group consisting of 5-[(4-phenylbutyl)methylamino]-2-(3,4-dimethoxyphenyl)-2-isopropylvaleronitrile and 5-[(5-phenylpentyl)methylamino]-2-(3,4-dimethoxyphenyl)-2-isopropylvaleronitrile.

2. Compound of claim 1 which is 5-[(4-phenylbutyl)methylamino]-2-(3,4-dimethoxyphenyl)-2-isopropylvaleronitrile, or a pharmaceutically acceptable salt thereof.

3. Compound of claim 1 which is 5-[(5-phenylpentyl)methylamino]-2-(3,4-dimethoxyphenyl)-2-isopropylvaleronitrile, or a pharmaceutically acceptable salt thereof.

4. A pharmaceutical composition comprising a therapeutically-effective amount of a calcium channel blocking compound and a pharmaceutically-acceptable carrier or diluent, said calcium channel blocking compound selected from 5-[(4-phenylbutyl)methylamino]-2-(3,4-dimethoxyphenyl)-2-isopropylvaleronitrile and 5-[(5-phenylpentyl)methylamino]-2-(3,4-dimethoxyphenyl)-2-isopropylvaleronitrile, or a pharmaceutically acceptable salt thereof.

5. The composition of claim 4 wherein said compound is 5-[(4-phenylbutyl)methylamino]-2-(3,4-dimethoxyphenyl)-2-isopropylvaleronitrile, or a pharmaceutically acceptable salt thereof.

6. The composition of claim 4 wherein said compound is 5-[(5-phenylpentyl)methylamino]-2-(3,4-dimethoxyphenyl)-2-isopropylvaleronitrile, or a pharmaceutically acceptable salt thereof.

7. A therapeutic method for treating hypertension, said method comprising administering to a hypertensive patient a therapeutically-effective amount of a compound selected from 5-[(4-phenylbutyl)methylamino]-2-(3,4-dimethoxyphenyl)-2-isopropylvaleronitrile and 5-[(5-phenylpentyl)methylamino]-2-(3,4-dimethoxyphenyl)-2-isopropylvaleronitrile, or a pharmaceutically acceptable salt thereof.

8. The method of claim 7 wherein said compound is 5-[(4-phenylbutyl)methylamino]-2-(3,4-dimethoxyphenyl)-2-isopropylvaleronitrile or, or a pharmaceutically acceptable salt thereof.

9. The method of claim 7 wherein said compound is 5-[(5-phenylpentyl)methylamino]-2-(3,4-dimethoxyphenyl)-2-isopropylvaleronitrile, or a pharmaceutically acceptable salt thereof.

* * * * *